United States Patent [19]

Schulsinger et al.

[11] Patent Number: 5,902,228
[45] Date of Patent: May 11, 1999

[54] METHOD AND APPARATUS FOR SUPPORT AND TUBULARIZATION OF SURGICAL GRAFTS

[75] Inventors: David A. Schulsinger, New York; Philip S. Li, Flushing; Marc Goldstein, New York, all of N.Y.

[73] Assignee: Cornell Research Foundation, Inc., Itaca, N.Y.

[21] Appl. No.: 08/940,959

[22] Filed: Oct. 8, 1997

Related U.S. Application Data

[60] Provisional application No. 60/027,915, Oct. 11, 1996.

[51] Int. Cl.[6] .......................................... A61F 2/04
[52] U.S. Cl. ................................ 600/36; 600/37; 623/11; 623/12; 128/897; 128/898
[58] Field of Search .......................... 600/37, 36; 623/11, 623/12; 128/897, 898

[56] References Cited

U.S. PATENT DOCUMENTS

| | | |
|---|---|---|
| 2,459,080 | 1/1949 | Killius . |
| 3,916,874 | 11/1975 | Perrin . |
| 4,144,744 | 3/1979 | Hill . |
| 4,239,492 | 12/1980 | Holman et al. . |
| 4,502,159 | 3/1985 | Woodroof et al. . |
| 4,681,588 | 7/1987 | Ketharanathan . |
| 4,773,418 | 9/1988 | Hettich . |
| 4,902,508 | 2/1990 | Badylak et al. . |
| 4,990,131 | 2/1991 | Dardik et al. . |
| 5,376,110 | 12/1994 | Tu et al. . |
| 5,498,257 | 3/1996 | Tebbetts . |

*Primary Examiner*—Robert L. Nasser
*Assistant Examiner*—Michael Astorino
*Attorney, Agent, or Firm*—Jones, Tullar & Cooper, P.C.

[57] ABSTRACT

The invention is directed to an apparatus and method for both supporting and preserving a piece of graft tissue during pre-implantation preparation, and for creating a tubular graft from the piece of graft tissue. The purpose of the device is (1) to support, stabilize, and preserve a piece of graft tissue; (2) to provide a rotating base to debride or otherwise prepare the donor tissue; and (3) to place the tissue around a mandrel for tubularization. The apparatus may be used as a support for preparing a piece of tissue for use as a skin graft or the like. Additionally, the preferred embodiment of the invention provides an advantageous method and apparatus for forming the graft tissue into a tubular configuration for use as a tubular graft.

20 Claims, 6 Drawing Sheets

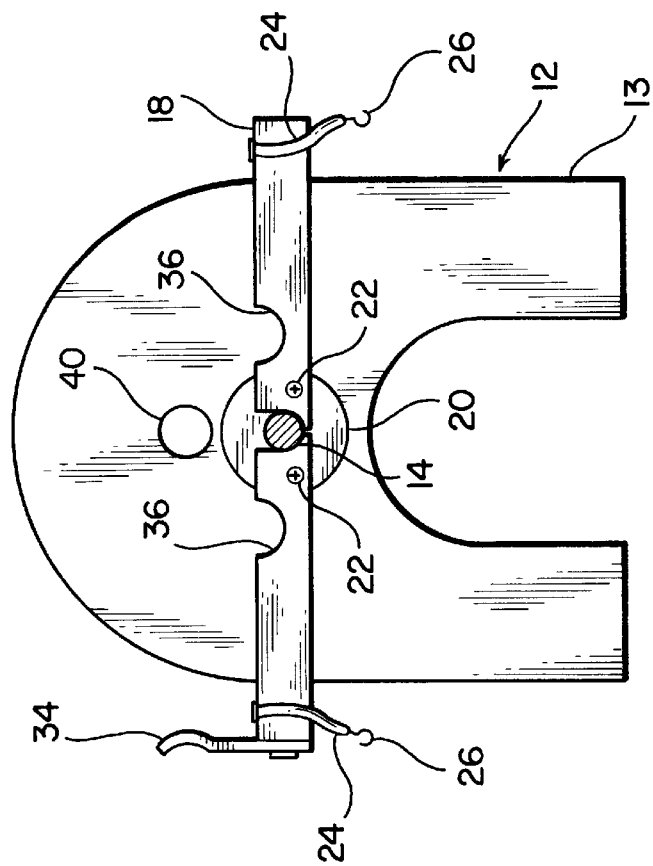
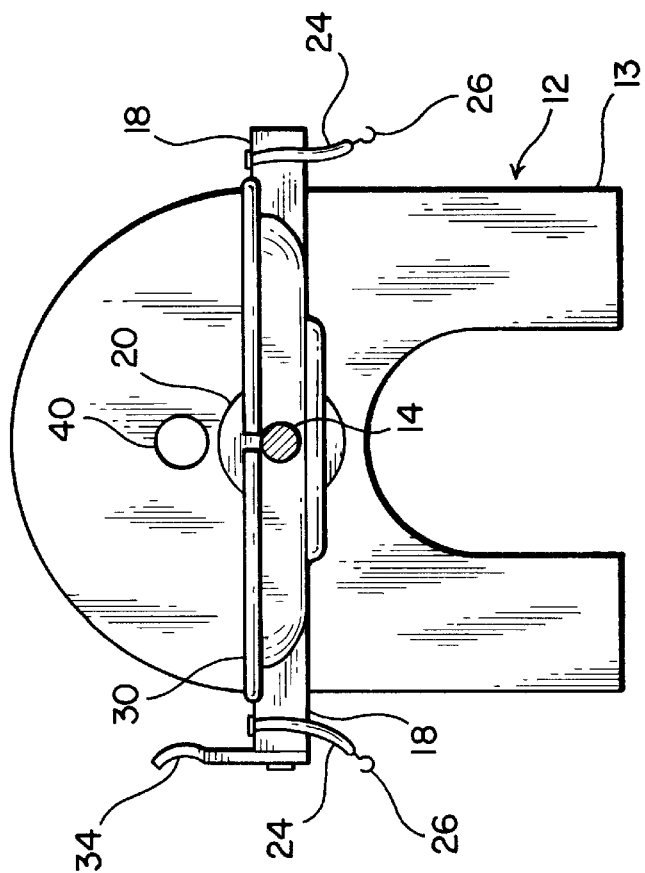

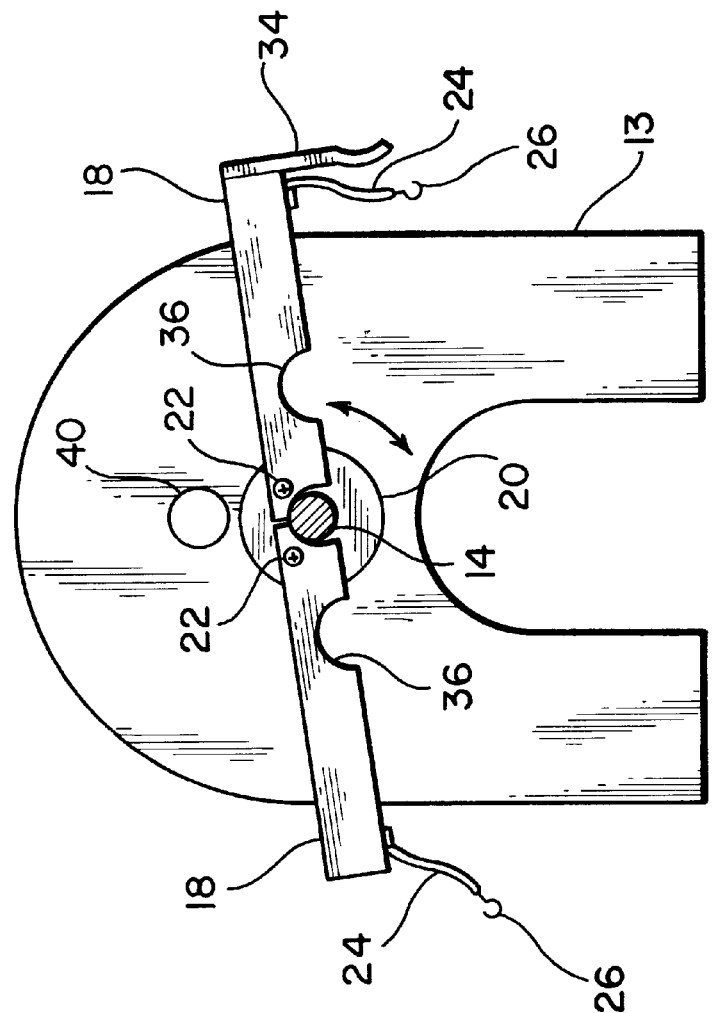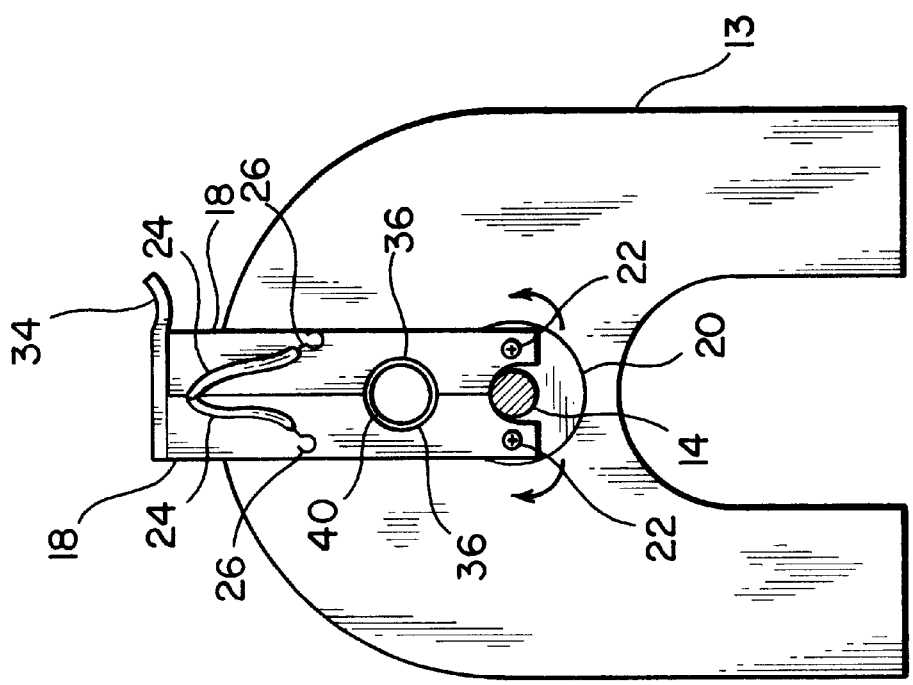

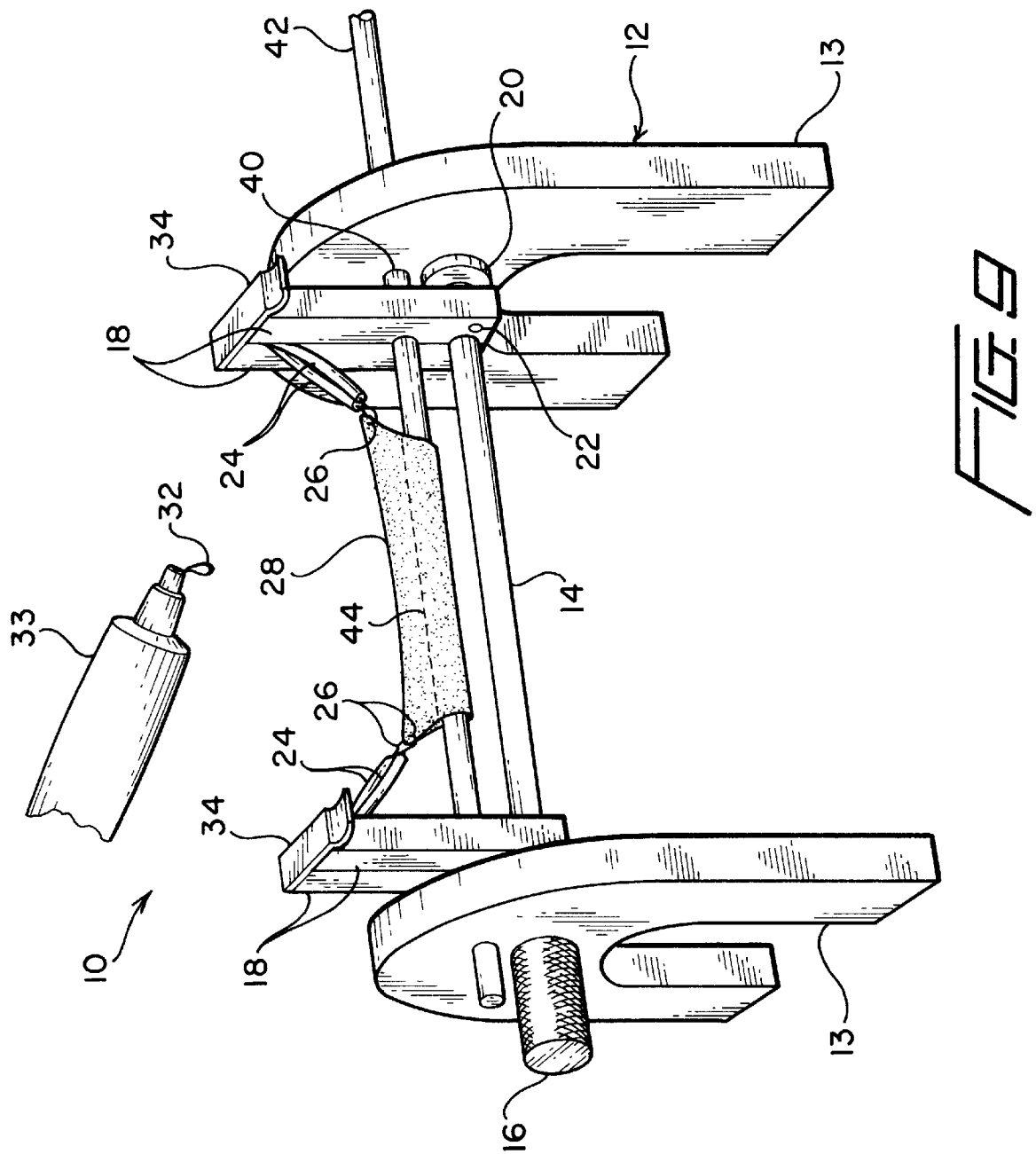

METHOD AND APPARATUS FOR SUPPORT AND TUBULARIZATION OF SURGICAL GRAFTS

CROSS-REFERENCE TO RELATED APPLICATION

This is a continuation-in-part of Ser. No. 60/027,915, filed on Oct. 11, 1996.

FIELD OF THE INVENTION

This invention is directed to a method and apparatus for supporting and preserving graft tissue during preparation for transplantation. This invention is also directed to a method and apparatus for forming tubular grafts for surgical use. The tubular grafts are useful for replacement or repair of tubular body parts, such as in the vascular system, the urinary tract, or the like.

DESCRIPTION OF THE PRIOR ART

Tubular grafts are widely used in modern surgery for replacement or repair of defective or diseased tubular body organs. The tubular grafts of the present invention may be used as grafts in the vascular system, the urinary tract, or as grafts for various other body sites. One particular use for the grafts of the present invention is in the treatment of hypospadias.

Hypospadias is a well recognized urologic congenital anomaly, occurring in 1 of 300 newborn boys, in which the urethral opening is formed at a point proximal to the distal end of the penis. In most instances, primary reconstruction can be accomplished with local penile and preputial skin. Occasionally, the pediatric urologist is confronted with the situation of deficient genital skin due to a prior operation or a high degree of urethral abnormality. In such instances, free extragenital non-hair-bearing skin tissue, bladder mucosa tissue, and buccal mucosa tissue have been used as grafts for forming a urethra. The graft tissue is autotransplanted into the penis to form a complete urethra.

SUMMARY OF THE INVENTION

The invention is directed to an apparatus and method for supporting and preserving a piece of graft tissue during pre-implantation preparation, and for creating a tubular graft from the piece of graft tissue. The apparatus of the present invention will be generally referred to as the Graft Tubularization Apparatus ("GTA"). The purpose of the device is (1) to support, stabilize and preserve a piece of graft tissue; (2) to provide a rotating base to debride and otherwise prepare the donor tissue; and (3) to place the tissue around a mandrel for tubularization whereby a piece of flat graft tissue is formed into a tubular configuration. The apparatus may be used as a support for preparing a piece of tissue for use as a flat skin graft or the like. However, the preferred embodiment of the invention provides an advantageous method and apparatus for forming the tissue into a tubular configuration.

The present invention is particularly useful in a two-step microsurgical procedure to correct hypospadias. A flat piece of graft tissue is first formed into a tubular configuration, and the tubular graft is then implanted as a urethral implant. Microsurgery is advantageous because it avoids large needle trauma, allows more precise apposition of the tissue, and identifies exact needle placement in the tissue.

The apparatus and method of the present invention makes the microsurgical hypospadias repair ("MHR") technique easier and quicker. It should be kept in mind, however, that the tubular grafts formed by using the present invention may be used at any place within the body where a tubular graft is desired. The invention is by no means limited only to forming tubular grafts for hypospadias repair.

BRIEF DESCRIPTION OF THE DRAWINGS

FIG. 5 is a view taken along line 5—5 of FIG. 4.

FIG. 6 is a view taken along line 6—6 of FIG. 4.

FIG. 7 is a view of FIG. 6 with the arms rotated into the folded position.

FIG. 8 is a view of FIG. 6 with the arms rotated about the cross bar.

FIG. 9 is a perspective view of the GTA showing a piece of graft tissue wrapped about the mandrel by rotating the arms into the folded position.

DESCRIPTION OF THE PREFERRED EMBODIMENT

The invention is directed to a method and apparatus for preserving graft tissue during preparation, and for forming tubular grafts for surgical use. In brief, the apparatus includes a base for supporting two pairs of opposed foldable arms. A hook or clip is connected to the end of each arm by an elastic cord, and a piece of graft tissue is supported by attaching a hook at each corresponding adjacent corner of the graft tissue, thereby suspending the tissue between the arms. To maintain the viability of the graft tissue, the tissue is supported in a tissue-preserving-medium chamber which bathes the tissue in a tissue-preserving medium for maintaining tissue viability.

Figure 1:
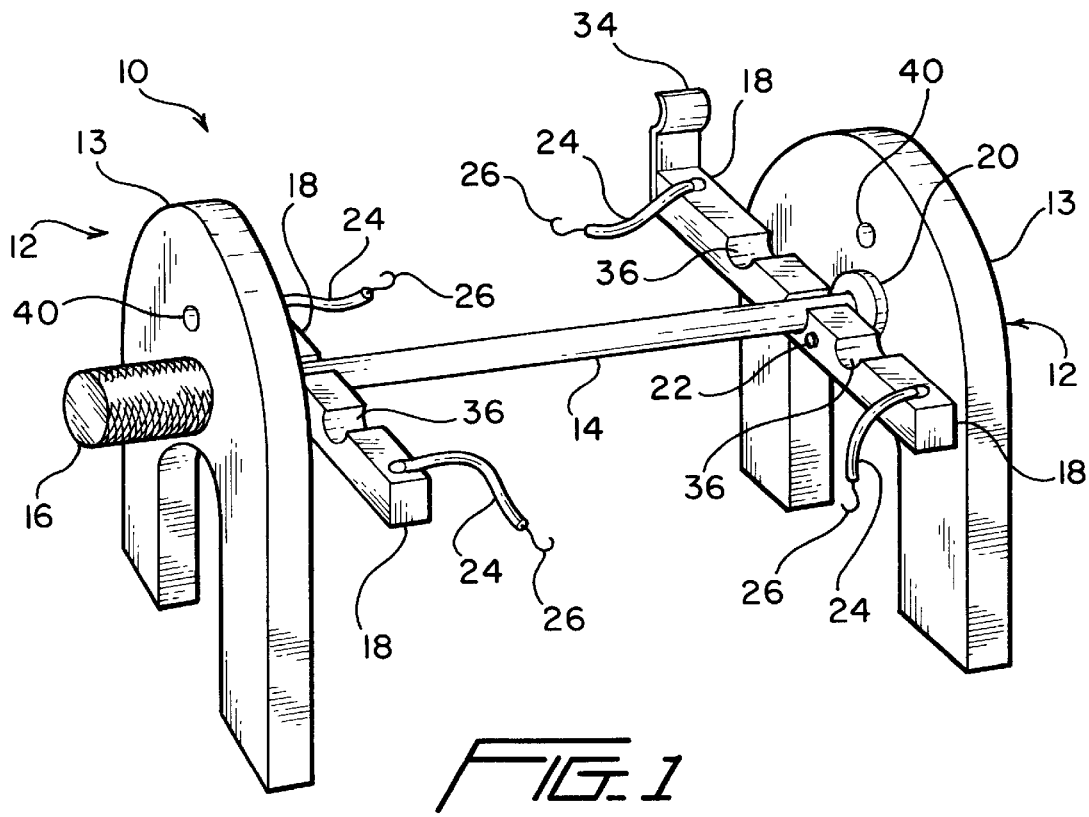
FIG. 1 is a perspective view of the GTA of the present invention.

As discussed above, the GTA device is useful for creating tubular grafts for microsurgical hypospadias repair, but also may be used for vascular grafts, skin grafts, or other applications requiring stabilization and preparation of graft tissue. In a preferred embodiment, referring to FIG. 1, the GTA, designated as item 10, includes a base 12 comprised of a pair of spaced arched members 13 connected by a cross bar 14. Cross bar 14 is connected between arched members 13 by thumb screws 16 which clamp arched members 12 against shoulders (not shown) on cross bar 14.

Four independently movable arms 18 are provided for supporting a piece of graft tissue between arched members 13. Arms 18 are mounted in two pairs on rotatable hubs 20. Rotatable hubs 20 are rotatably mounted on arched members 13 for rotation about the axis of cross bar 14. Furthermore, arms 18 are mounted on hubs 20 by arm-mounting screws 22. Each arm 18 may be rotated approximately 90 degrees about the axis of arm-mounting screw 22 from an extended position, as illustrated in FIG. 6, to a folded position, as illustrated in FIG. 7. Furthermore, each pair of arms 18 may be rotated as a unit 360 degrees (in either the folded or extended position) by rotating rotatable hub 20 in either direction about the axis of cross bar 14, as illustrated in FIG. 8.

Figure 2:
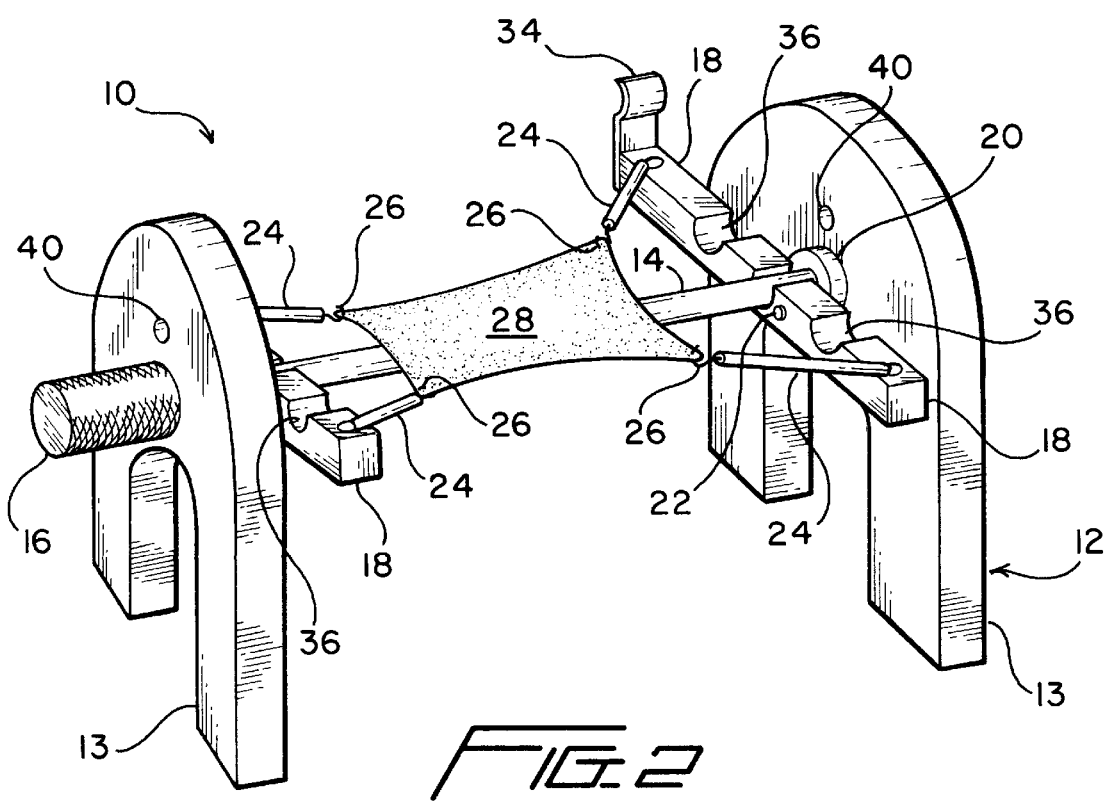
FIG. 2 is a perspective view of the GTA with a piece of graft tissue suspended therein.

An elastic band 24 or similar resilient connector is attached to the free end of each arm 18, and a hook, clip, or similar gripping device 26 is attached to the end of each elastic band 24 for gripping a corresponding adjacent corner of a piece of graft tissue 28, as illustrated in FIG. 2. Graft tissue 28 is most useful in the present invention if it is in a generally rectangular shape, as illustrated in FIG. 2, so that a hook 26 (four in total) may be attached to each corner of tissue 28, thereby suspending tissue 28 in a generally stretched configuration between arms 18.

Figure 3:
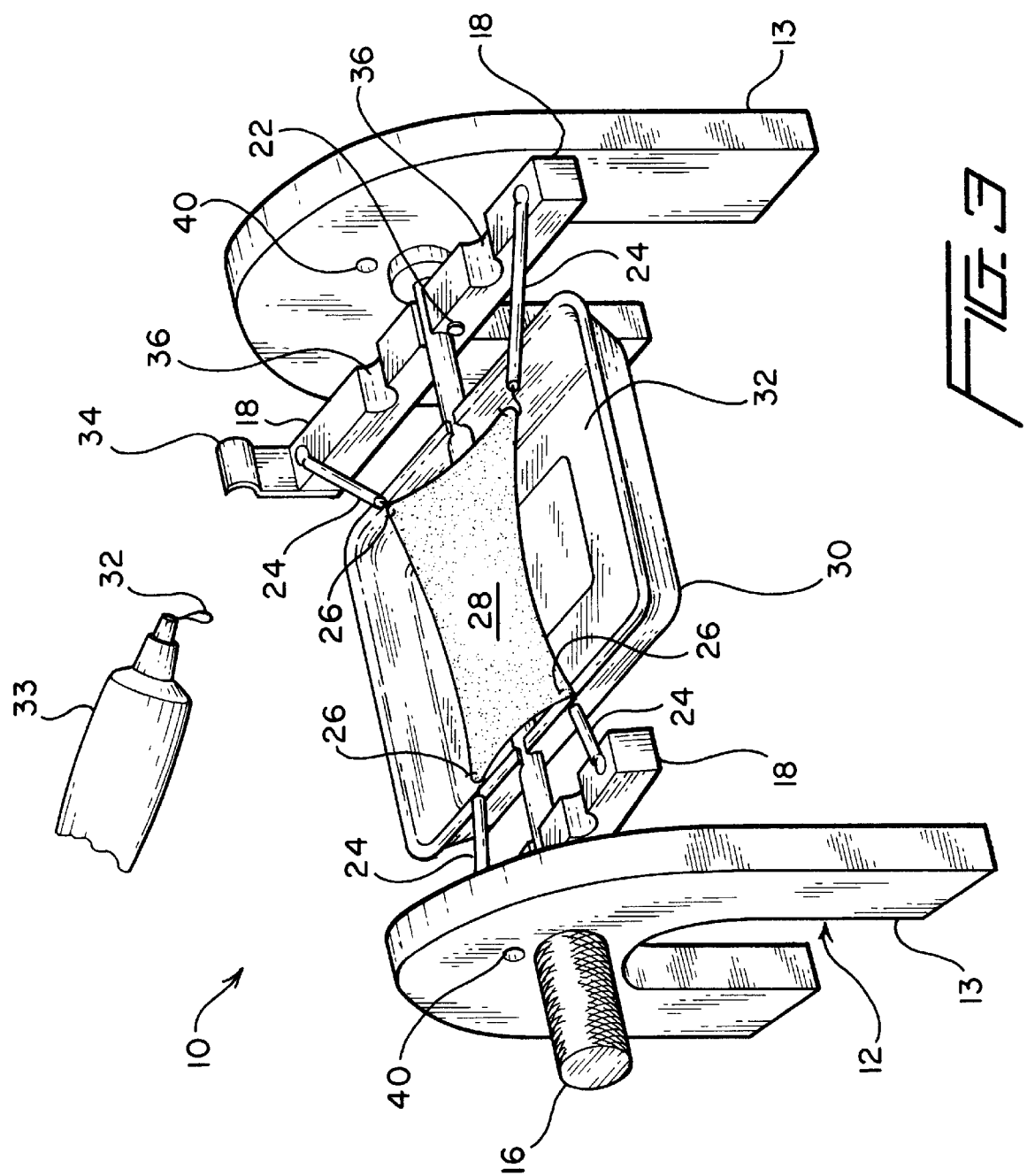
FIG. 3 is a perspective view of the GTA with a piece of graft tissue suspended therein and the tissue-preserving medium chamber mounted on the cross bar.
Figure 4:
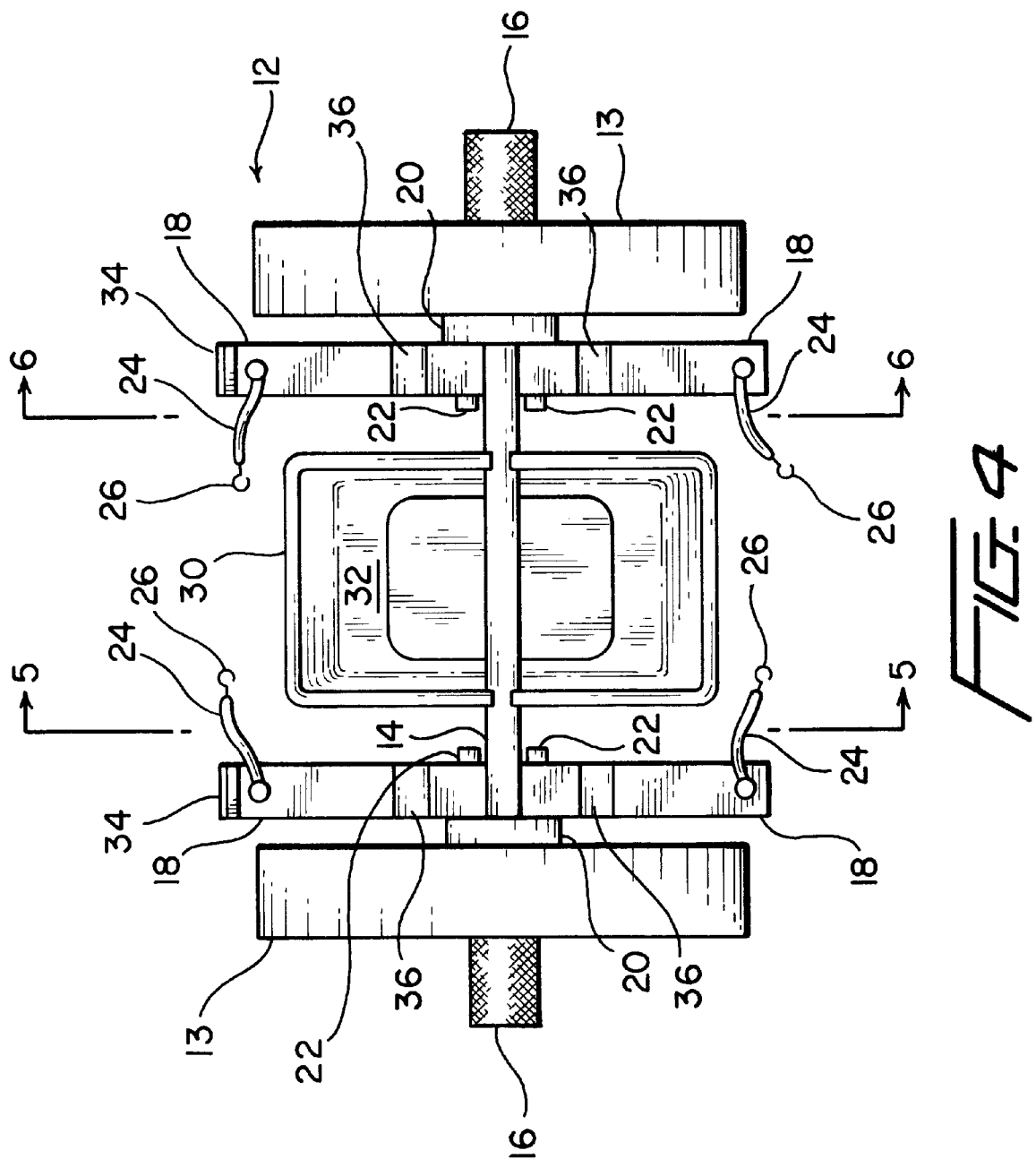
FIG. 4 is a top view of the GTA with the tissue-preserving medium chamber mounted on the cross bar.

As illustrated in FIGS. 3, 4, and 5, a chamber 30 for containing a tissue preserving medium 32 may be removably mounted on cross bar 14. Tissue preserving medium 32, which is preferably buffered, bathes graft tissue 28 to maintain its viability during cleaning, debriding, or other preparation. The tissue preserving medium 32 is preferably PEDIC-URO MHR™, a buffered tissue preserving medium which is described in Provisional Patent Application Ser. No. 60/027,935 and in the corresponding non-provisional patent application filed concurrently herewith Ser. No. 08/946,936 by the inventors herein, entitled "Preserving Tissue", the disclosures of which are incorporated herein by reference. Of course alternative tissue preserving media may also be used, so long as they serve to maintain the viability of graft tissue 28.

One arm 18 of each pair of arms 18 has a clip 34 mounted on the distal end thereof. As shown in FIGS. 7 and 9, clip 34 retains a pair of arms 18 in the folded position when they are rotated to be adjacent one-another. Arms 18 also include semicircular cut-outs 36. When arms 18 are rotated to a folded vertical position, as shown in FIG. 7, cut-outs 36 create a hole through the folded arms 18. This hole matches up with a mandrel hole 40 formed through each arched member 13.

As illustrated in FIG. 9, a mandrel 42 may be passed through mandrel holes 40. Graft tissue 28 is then wrapped around mandrel 42 by moving arms 18 into the folded position. The graft tissue 28 may then be tubularized by suturing the edges of graft tissue 28 together, as shown at 44. The suturing is advantageously performed using a non-traumatic microsurgical needle, as described in Provisional Patent Application Ser. No. 60/027,910 and in the corresponding non-provisional patent application filed concurrently herewith Ser. No. 08/940,960, by the inventors herein, entitled "MICROSURGICAL SUTURE NEEDLE", the disclosures of which are incorporated herein by reference.

In use, after harvesting the graft tissue 28 from the donor site (i.e., bladder, buccal mucosa, or the like), the graft tissue 28 (preferably 2–4 cm by 1.5–2.5 cm for MHR) is suspended in the GTA 10 by elastic bands 24 and hooks 26 in each corner, as illustrated in FIG. 2. Medium chamber 30 may then be mounted on cross bar 14 and filled with PEDIC-URO MHR™ or other tissue preserving medium 32 so that the underside of tissue 28 is in contact with the preserving medium 32, whereby the preserving medium 32 osmoses into tissue 28. The upper side of tissue 28 is occasionally irrigated or sprayed with additional preserving medium 32 using a 10 cc irrigation syringe 33 or other suitable means. In this manner the viability of tissue 28 is maintained while the graft is suspended in the GTA, as illustrated in FIG. 3.

The upper surface of tissue 28 may then be cleaned, debrided, or otherwise prepared. Medium chamber 30 may then be removed from cross bar 14, and arms 18 rotated about the axis of cross bar 14 in order to rotate the suspended graft 180°. Medium chamber 30 may then be replaced on cross bar 14 so that the tissue 28 may be contacted by medium solution 32 while the underside of tissue 28 is cleaned, debrided, or otherwise prepared. If the tissue is to be used as a flat graft, such as a skin graft, the tissue is then ready to be implanted into the patient.

However, the present invention also provides an advantageous means for forming the tissue into a tubular implant. Thus, following preparation, graft tissue 28 is rotated again 180° to assume its original position. Mandrel 42 is then introduced through mandrel holes 40, immediately superior and parallel to graft tissue 28. A catheter of suitable diameter may be used for mandrel 42, or any other suitable sterile elongate cylindrical or tapered article of the desired diameter may suffice.

Graft tissue 28 is then folded at least partially around mandrel 42 by rotating each pair of arms 18 ninety degrees toward each other so that they assume a vertical folded position, as illustrated in FIG. 9. This position allows the graft to be tubularized by suturing with sutures 44 or by other equivalent techniques. The suturing may advantageously be carried out using the non-traumatic microsurgical suture needle referenced above, or by other suitable means. During suturing, graft tissue 28 is kept viable by occasional irrigation with preserving medium 32. Following suturing, graft tissue 28 is removed from mandrel 42 and is ready for implantation.

EXAMPLE

The patient is a newborn boy with hypospadias and particularly with a urethral opening on the underside of the penis at a point proximal to the distal end of the penis.

A piece of tissue for autotransplantation grafting is obtained from the patient as follows: The inside of a cheek is sterilized by the application of betadine and isolated sterilely. A surgical knife with a 15 degree blade is used to remove from the sterilized isolated inner portion of the cheek, a generally rectangular surface flat piece of buccal mucosal tissue 28 of dimensions 2 by 4 cm by 1 to 2 mm thick.

The removed piece of graft tissue 28 is quickly (about 1 second) transferred with tissue forceps into the tissue-preserving-medium chamber 30 of GTA 10 that is filled with tissue preserving medium 32 of composition designated above as PEDIC-URO MHR™. The graft tissue 28 is maintained in contact with said tissue preserving medium 32 while elastic bands 24 and hooks 26 are connected to the corresponding adjacent corners of tissue 28.

The tissue 28 is initially suspended on the GTA 10 in contact with tissue preserving medium 32 in a generally flat, horizontal orientation, suspended by elastic bands 24 and hooks 26, as illustrated in FIG. 3. The mucosa side of tissue 28 is facing upwards at this point, and the cut side is facing downward. The upper side of tissue 28 is cleaned or otherwise prepared, and additional preserving medium is occasionally irrigated onto the upper side, as required to maintain the viability of tissue 28.

Following preparation of the upper side of tissue 28, chamber 30 is removed from cross bar 14, and arms 18 are rotated 180 degrees so that the cut side of tissue 28 is facing upward. Chamber 30 is placed back onto cross bar 14 so that tissue 28 is in contact with tissue preserving medium 32. The cut side of tissue 28 is next cleaned and debrided so that the entire tissue 28 is of a uniform desired thickness. Tissue 28 is occasionally irrigated with preserving medium 30, as required to maintain viability.

After cleaning and debriding of tissue 28, arms 18 are rotated back around so that the mucosa side of tissue 28 is again facing upward. Mandrel 42 is inserted into mandrel holes 40, and each pair of arms 18 are folded toward each other. In this manner tissue 28 is wrapped around mandrel 42, with the long sides of the rectangle being brought into butting relation as illustrated in FIG. 9.

The tubularization is completed by suturing the long sides together using 9-O vicryl suture material to form sutures 44. During suturing, the tissue piece 28 is maintained in a viable state by continual irrigation with preserving medium 32 using irrigation syringe 33 or the like. The suturing is carried out with the above-referenced non-traumatic microsurgical needle. Excess tissue edges may be trimmed from the sutured junction using microsurgical scissors or the like. The time from removal of the piece of buccal mucosa tissue to completion of tubularization is about 30 minutes.

The penis is then reconstructed as follows: The penis is cut open axially using a scalpel, and the now tube-shaped piece of graft material 28 is removed from the graft tubularization apparatus by sliding out mandrel 42. Graft tissue 28 is positioned axially in the opened penis so that one end contacts native urethra. After the insertion of a catheter through the passage of the tube of graft tissue 28 and into the native urethra, graft tissue 28 is anastomosed to the native urethra by suturing with 9-O vicryl suture material to create a new urethra meatus. The penis is then sutured together along its length with said microsurgical suture needle to complete the reconstruction procedure. During the course of the reconstruction, the graft tissue is kept moist and viable by irrigation with the tissue preserving medium 32 using syringe 33. Following surgery, the sutures gradually dissolve. The catheter bridging the anastomosis is removed after seven days and the patency of anastomosis is maintained.

It may be seen that the importance of the GTA is to provide a stabilized stationary base to debride graft tissue after harvesting and to prepare the tissue for tubularization by microsurgery. The usefulness of the GTA is not limited to pediatric urology, but it can be used by any surgeon requiring stabilization and preparation of graft tissue. Therefore, a plastic surgeon could use this device for a preparing a planar skin graft, while a vascular surgeon may use this device for preparing a tubular vascular graft.

If the GTA is to be used solely for preparing planar pieces of graft tissue for use a skin grafts or the like, then the folding feature of arms 18 may be eliminated, and two spaced arms having two free ends substituted. Of course, a number of other structural modifications may be made to the GTA and still be within the scope of the disclosed invention. For example, the two arched members 13 of base 12 could be replaced with a single contiguous base unit having a pair of uprights for supporting arms 18. Under this configuration, cross bar 14 could also be eliminated, and chamber 30 supported by a stand or the like. Additional structural modifications will be apparent to those skilled in the art.

The information discussed above describes the preferred apparatus and method for practicing the present invention. The GTA significantly simplifies the process of preparing tissue for tubularization and it also saves time during surgical procedures. The goal of the GTA is to allow a surgeon to perform a grafting procedure in a more precise and expeditious manner.

Although preferred embodiments of the invention have been described herein in specifics, the use of those specifics is not intended to limit the invention in any way. It will be recognized that a variety of changes may be made, and equivalent structures adopted, without departing from the spirit of the invention that is intended to be covered by this patent.

What is claimed is:

1. An apparatus for supporting and preserving tissue in preparation for transplantation of the tissue, said apparatus comprising:
   a base, said base supporting at least two spaced support arms for supporting the tissue, such that the tissue may be supported between said arms, and
   a chamber located between said arms, said chamber containing a tissue preserving medium, such that the tissue is supported between said arms and in contact with said tissue-preserving medium, whereby said tissue preserving medium helps maintain the tissue in a viable state during preparation for transplantation.

2. The apparatus of claim 1 in which said base includes a pair of spaced arch members.

3. The apparatus of claim 1 in which said arms are mounted on an elongate crossbar, said arms being rotatable at least 180 degrees about the axis of said cross bar, and thereby being able to rotate the tissue.

4. The apparatus of claim 3 in which said crossbar supports said chamber.

5. The apparatus of claim 1 in which said arms include two spaced pairs of arms, with the arms of each said pair of arms being foldable toward each other.

6. The apparatus of claim 5 further including a mandrel, said mandrel being located above said cross bar such that when said arms are folded, said tissue at least partially wraps around said mandrel to facilitate tubularization of said tissue.

7. The apparatus of claim 6 further including a resilient band mounted on the end of each arm, said band being connectable to a corresponding adjacent portion of the tissue for supporting the tissue.

8. An apparatus for forming a piece of flat tissue into a tubular configuration, said apparatus comprising:
   a base, said base supporting two spaced pairs of arms, each said pair of arms including two arms foldable toward each other, said two spaced pairs of arms being capable of supporting a piece of tissue therebetween; and
   a mandrel mounted on said base whereby when said arms of said pairs are folded, said tissue wraps at least partially around said mandrel for facilitating the formation of said tissue into a tubular configuration.

9. The apparatus of claim 8 further including a chamber containing tissue preserving medium positioned between said spaced pairs of arms, such that the tissue is in contact with said medium.

10. The apparatus of claim 9, further including an elongate crossbar, said crossbar supporting said chamber and said two spaced pairs of arms.

11. The apparatus of claim 10 in which said arms may be rotated at least 180 degrees by rotating about the axis of said crossbar, whereby said tissue may be rotated at least 180 degrees.

12. The apparatus of claim 11 in which said base includes a spaced pair of arched base members, said arms and said crossbar being disposed between said arched members.

13. The apparatus of claim 12 in which each of said arms include a resilient band attached to the free end thereof, each said band also being connectable to the tissue for supporting the tissue.

14. The apparatus of claim 13 further including hooks for connecting said bands to the tissue.

15. A method of preserving and preparing a piece of tissue for transplantation, said method comprising:
   harvesting a piece of tissue from a donor site; and supporting said piece of tissue between two spaced pairs of arms, said tissue also being in contact with a tissue preserving medium, whereby said tissue may be debrided or otherwise prepared while in contact with said tissue preserving medium.

16. The method of claim 15 further including the step of folding each pair of said arms toward each other so that said tissue wraps at least partially around a mandrel, whereby formation of said tissue into a tubular configuration is facilitated.

17. The method of claim 16 further including the step of suturing said tissue about said mandrel for forming said tissue into a tubular graft.

18. The method of claim 15 further including the step of rotating said arms 180 degrees to debride or otherwise prepare the underside of said tissue prior to tubularization of said tissue.

19. The method of claim 15 in which said tissue preserving medium is PEDIC-URO MHR™.

20. The method of claim 15 further wherein said contacting said tissue with a tissue preserving medium includes the step of irrigating said tissue with said medium using a syringe.

* * * * *